United States Patent
Atwood et al.

(10) Patent No.: US 11,439,668 B2
(45) Date of Patent: Sep. 13, 2022

(54) METHODS TO DIFFERENTIATE STEM CELLS INTO HORMONE-PRODUCING CELLS

(71) Applicant: JangoBio, LLC, Madison, WI (US)

(72) Inventors: Craig S. Atwood, Fitchburg, WI (US); Sivan Vadakkadath Meethal, Madison, WI (US)

(73) Assignee: JangoBio, LLC, Madison, WI (US)

( * ) Notice: Subject to any disclaimer, the term of this patent is extended or adjusted under 35 U.S.C. 154(b) by 0 days.

(21) Appl. No.: 15/947,304

(22) Filed: Apr. 6, 2018

(65) Prior Publication Data

US 2018/0221419 A1    Aug. 9, 2018

Related U.S. Application Data

(63) Continuation-in-part of application No. 14/718,390, filed on May 21, 2015, now Pat. No. 11,253,549.

(60) Provisional application No. 62/002,305, filed on May 23, 2014.

(51) Int. Cl.
| | |
|---|---|
| *A61K 35/545* | (2015.01) |
| *A61K 35/52* | (2015.01) |
| *A61K 35/55* | (2015.01) |
| *A61P 5/24* | (2006.01) |
| *A61P 5/06* | (2006.01) |
| *C07K 14/59* | (2006.01) |
| *A61K 35/54* | (2015.01) |
| *A61K 35/15* | (2015.01) |
| *A61K 31/568* | (2006.01) |
| *A61K 31/566* | (2006.01) |
| *A61K 31/57* | (2006.01) |
| *A61K 9/00* | (2006.01) |

(52) U.S. Cl.
CPC .......... *A61K 35/545* (2013.01); *A61K 31/566* (2013.01); *A61K 31/568* (2013.01); *A61K 31/57* (2013.01); *A61K 35/15* (2013.01); *A61K 35/52* (2013.01); *A61K 35/54* (2013.01); *A61K 35/55* (2013.01); *A61P 5/06* (2018.01); *A61P 5/24* (2018.01); *C07K 14/59* (2013.01); *A61K 9/0019* (2013.01)

(58) Field of Classification Search
CPC ...... A61K 35/545; A61K 35/52; A61K 35/55; A61K 35/54; A61K 31/568; A61K 31/566; A61K 31/57; A61K 35/15; A61K 9/0019; A61P 5/24; A61P 5/06; C07K 14/59
See application file for complete search history.

(56) References Cited

U.S. PATENT DOCUMENTS

| | | | |
|---|---|---|---|
| 6,503,894 B1 | 1/2003 | Dudley et al. | |
| 7,361,505 B1 | 4/2008 | Weiss et al. | |
| 7,368,115 B2 | 5/2008 | Ohta et al. | |
| 7,595,056 B1 | 9/2009 | Mendis-Handagama et al. | |
| 7,674,457 B2 | 3/2010 | Borlongan et al. | |
| 7,700,352 B2 | 4/2010 | Niwa et al. | |
| 7,846,898 B2 | 12/2010 | Weiss et al. | |
| 8,137,662 B2 | 3/2012 | Freeman et al. | |
| 8,143,220 B2 | 3/2012 | Weiss et al. | |
| 8,217,002 B2 | 7/2012 | Weiss et al. | |
| 8,435,949 B2 | 5/2013 | Weiss et al. | |
| 8,603,809 B2 | 12/2013 | Kruse | |
| 8,658,128 B2 | 2/2014 | Altschul et al. | |
| 2002/0168350 A1 | 11/2002 | Brazelton et al. | |
| 2003/0027804 A1 | 2/2003 | Van Der Hoop | |
| 2003/0100997 A1 | 5/2003 | Dunnington et al. | |
| 2004/0115175 A1 | 6/2004 | Blau et al. | |
| 2006/0234918 A1 | 10/2006 | Gregory et al. | |
| 2007/0026520 A1 | 2/2007 | Kelly | |
| 2007/0128174 A1 | 6/2007 | Kleinsek et al. | |
| 2007/0166289 A1 | 7/2007 | Hathaway et al. | |
| 2007/0179092 A1 | 8/2007 | Ohta et al. | |
| 2008/0280360 A1 | 11/2008 | Kaplan et al. | |
| 2009/0099623 A1 | 4/2009 | Bentwich | |
| 2009/0105521 A1 | 4/2009 | Bentwich | |
| 2009/0197796 A1 | 8/2009 | Gregory et al. | |
| 2009/0274668 A1 | 11/2009 | Thompson et al. | |
| 2010/0028361 A1 | 2/2010 | Smith et al. | |
| 2010/0034779 A1 | 2/2010 | Guan et al. | |
| 2010/0062477 A1 | 3/2010 | Yu | |
| 2010/0135980 A1 | 6/2010 | Rodriguez | |
| 2010/0173344 A1 | 7/2010 | Yu | |
| 2010/0310532 A1 | 12/2010 | Hare et al. | |
| 2011/0081323 A1 | 4/2011 | Kleinsek et al. | |
| 2011/0104100 A1 | 5/2011 | Riordan et al. | |
| 2011/0286998 A1 | 11/2011 | Gregory et al. | |
| 2011/0293685 A1 | 12/2011 | Kuo et al. | |

(Continued)

FOREIGN PATENT DOCUMENTS

| | | |
|---|---|---|
| WO | 2013065763 A1 | 5/2013 |
| WO | 2017048193 A1 | 3/2017 |

OTHER PUBLICATIONS

Del Tredici et al. Identification of the First Synthetic Steroidogenic Factor 1 Inverse Agonists: Pharmacological Modulation of Steroidogenic Enzymes. Molecular Pharmacology (2008), 73(6), 900-908. (Year: 2008).*

(Continued)

*Primary Examiner* — Sean C. Barron
(74) *Attorney, Agent, or Firm* — IceMiller LLP

(57) ABSTRACT

Methods are described for differentiating stem and postnatal cells into sex hormone-producing cells that can be administered to a patient autologously or allogeneically in order to maintain in balance, or rebalance, their hypothalamic-pituitary-gonadal (HPG) axis.

5 Claims, 3 Drawing Sheets

(56) References Cited

U.S. PATENT DOCUMENTS

| | | |
|---|---|---|
| 2011/0312091 A1 | 12/2011 | Zhao et al. |
| 2012/0070445 A1 | 3/2012 | Smith et al. |
| 2012/0276070 A1 | 11/2012 | Musick |
| 2012/0322856 A1 | 12/2012 | Dimmeler et al. |
| 2013/0243739 A1 | 9/2013 | Burt |
| 2015/0359822 A1 | 12/2015 | Atwood |
| 2018/0221419 A1 | 8/2018 | Atwood et al. |

OTHER PUBLICATIONS

Whitby et al. (Journal of Medicinal Chemistry (2011), 54, 2266-2281. Small Molecule Agonists of the Orphan Nuclear Receptors Steroidogenic Factor-1 (SF-1, NR5A1) and Liver Receptor Homologue-1 (LRH-1, NR5A2). (Year: 2011).*

Chen et al. Wt1 directs the lineage specification of sertoli and granulosa cells by repressing Sf1 expression. Development (Jan. 2017), 144, 44-53. (Year: 2017).*

Chen et al. Stem Leydig Cells: From Fetal to Aged Animals. Birth Defects Res C Embryo Today (2010), 90(4), 21 page reprint. (Year: 2010).*

Hummitzsch et al. Stem Cells, Progenitor Cells, and Lineage Decisions in the Ovary. Endocrine Reviews (2015), 36(1), 65-91. (Year: 2015).*

Hormone (The Macmillan Encyclopedia (2003), 1 page. (Year: 2003).*

Tosh et al. Conversion of pancreatic cells to hepatocytes. 2002, Biochem Soc Trans 30: 51-55. (Year: 2002).*

Castro et al. Failure of Bone Marrow Cells to Transdifferentiate into Neural Cells in Vivo. 2002, Science 297: 1299 (Year: 2002).*

Mezey et al. and Castro et al. (Science (2003), 299, 1184b-c. (Year: 2003).*

Reinecke et al. Skeletal Muscle Stem Cells Do Not Transdiferentiate Into Cardiomyocytes After Cardiac Grafting. 2002, J Mol Cell Cardiol 34: 241-249. (Year: 2002).*

Murry et al. Haematopoietic stem cells do not transdifferentiate into cardiac myocytes in myocardial Infarcts. 2004, Nature 428: 664-668 (Year: 2004).*

Hynes K., Menicanin D., Gronthos S., Bartold M.P. (2014) Differentiation of iPSC to Mesenchymal Stem-Like Cells and Their Characterization. In: Turksen K., Nagy A. (eds) Induced Pluripotent Stem (iPS) Cells. Methods in Molecular Biology, vol. 1357. Humana Press, New York, NY (Year: 2014).*

S. S. Negus. Some implications of receptor theory for in vivo assessment of agonists, antagonists and inverse agonists. Biochemical Pharmacology (2006), 71, 1663-1670. (Year: 2006).*

Passweg et al. Hematopoietic stem cell transplantation: a review and recommendations for follow-up care for the general practitioner. Swiss Med Wkly (2012), 142, w13696, 15 pages. (Year: 2012) [Cited in related U.S. Appl. No. 14/718,390].

Wei et al. Mesenchymal stem cells: a new trend for cell therapy. Acta Pharmacol Sin (2013); 34(6), 747-754. (Year: 2013) [Cited in related U.S. Appl. No. 14/718,390].

Lim et al. Hematopoietic cell differentiation from embryonic and induced pluripotent stem cells. Stem Cell Res Ther (2013)4(3), 11 pages. (Year: 2013) [Cited in related U.S. Appl. No. 14/718,390].

Xu et al. Concise Review: Chemical Approaches for Modulating Lineage-Specific Stem Cells and Progenitors. Stem Cells Translational Medicine (2013), 2, 355-361. (Year: 2013) [Cited in related U.S. Appl. No. 14/718,390].

Poumasr et al. Concise Review: Alchemy of Biology: Generating Desired Cell Types from Abundant and Accessible Cells. Stem Cells (2011), 29, 1933-1941. (Year: 2011) [Cited in related U.S. Appl. No. 14/718,390].

Guiterrez-Aranda et al. Human Induced Pluripotent Stem Cells Develop Teratoma More Efficiently and Faster Than Human Embryonic Stem Cells Regardless the Site of Injection. Stem Cells (2010), 28(9), p. 1568-1570. (Year: 2010) [Cited in related U.S. Appl. No. 14/718,390].

Blum et al. The tumorigenicity of human embryonic stem cells . . . Adv. Cancer Res. (2008), 100, 133-158, Abstract only. (Year: 2008) [Cited in related U.S. Appl. No. 14/718,390].

Sun et al. Leydig cell transplantation restores androgen production in surgically castrated prepubertal rats. Asian Journal of Andrology (2009), v11, pp. 405-109 [Cited in related U.S. Appl. No. 14/718,390].

Durruthy et al. Fate of induced pluripotent stem cells following transplantation to murine seminiferous tubules. Human Molecular Genetics (epub. Jan. 2014), v23(12), pp. 3071-3084 [Cited in related U.S. Appl. No. 14/718,390].

Manzoor et al. Serum Inhibin B as a D Iagnostic Marker of Male Infert Ility. J Ayub Med Coll Abbottabad (2012), v24(3-4), pp. 113-116 [Cited in related U.S. Appl. No. 14/718,390].

Chatterjee et al. Patterns of Leydig cell insufficiency in adult males following bone marrow transplantation for haematological malignancies. Bone Marrow Transplant (2001), v28(5), pp. 497-502 [Cited in related U.S. Appl. No. 14/718,390].

Shores et al. Testosterone Treatment and Mortality in Men with Low Testosterone Levels. J Clin Endocrinol Metab (2012), v97(6), p. 2050-2058 [Cited in related U.S. Appl. No. 14/718,390].

Chen et al., "Wt1 Directs the Lineage Specification of Sertoli and Granulosa Cells by Repressing Sf1 Expression," The Company of Biologists, Development, 2017, vol. 144, No. 1, pp. 44-53.

Atwood et al. "Does the Degree of Endocrine Dyscrasia Post-Reproduction Dictate Post-Reproductive Lifespan? Lessons from Semelparous and Iteroparous Species" GeroScience, 2017, vol. 39, pp. 103-116.

Veiga-Lopez et al. "Developmental Programming: Prenatal Testosterone Excess Disrupts Anti-Mullerian Hormone Expression in Preantral and Antral follicles," Fertility and Sterility, Mar. 2012, vol. 97, No. 3, pp. 748-756.

Yonker et al. "Hypothalamic-Pituitary-Gonadal Axis Homeostasis Predicts Longevity," Age, 2013, vol. 35, No. 1, pp. 129-138.

Zang et al. "Transplantation of CD51+ Stem Leydig Cells: A New Strategy for the Treatment of Testosterone Deficiency," Stem Cells, 2017, vol. 35, No. 5, pp. 1222-1232.

International Search Report and Written Opinion issued in PCT/US2019/026305, dated Jul. 11, 2019.

Yazawa, et al. "Differentiation of mesenchymal stem cells into gonad and adrenal steroidogenic cells" World Journal of Stem Cells, vol. 6, No. 2, Apr. 26, 2014, pp. 203-212.

Fu et al. Regenerative medicine: Transdifferentiation in vivo. Cell Research (2013), 24, 141-142. (Year: 2014) [Cited in related U.S. Appl. No. 14/718,390].

M.K. Drawer. Testosterone Replacement in Men With Andropause: An Overview. Rev. Ural. (2004), 6(Suppl. 6), S9-S15. (Year: 2004) [Cited in related U.S. Appl. No. 14/718,390].

European Patent Application No. 19781961.8; Extended Search Report; dated Dec. 7, 2021; 9 pages.

Atwood et al.; "Dysregulation of the Hypothalamic-Pituitary-Gonadal Axis with Menopause and Andropause Promotes Neurodegenerative Senescence"; Journal of Neuropathology & Experimental Neurology; vol. 64 No. 2; Feb. 2005; p. 93-103.

* cited by examiner

METHODS TO DIFFERENTIATE STEM CELLS INTO HORMONE-PRODUCING CELLS

CROSS-REFERENCE TO RELATED APPLICATION

This application is a Continuation-in-part application and claims priority to U.S. patent application Ser. No. 14/718,390, filed on May 21, 2015, titled, "METHODS TO REBALANCE THE HYPOTHALAMIC-PITUITARY-GONADAL AXIS" which claims priority to U.S. Provisional Application Ser. No. 62/002,305, filed on May 23, 2014, titled, "METHODS TO REBALANCE THE HYPOTHALAMIC-PITUITARY-GONADAL AXIS: APPLICATIONS IN DELAYING AGE-RELATED DISEASES AND EXTENSION OF LONGEVITY", the disclosures of which are incorporated herein by reference in their entireties.

FIELD OF THE INVENTION

The present invention relates to drugs and methods to differentiate stem cells into sex hormone-producing cells. More particularly, the disclosure relates to specific compounds and combinations of these compounds for improving sex hormone production from cells differentiated using such treatments.

BACKGROUND OF THE INVENTION

Stem cells have the potential to self-renew (divide) and differentiate into specialized cell types.

Mesenchymal stem cells (MSC) are a group of clonogenic cells capable of self-renewal and differentiation displaying phenotypic characteristics of multilineage mesoderm-type cells, such as osteoblasts, adipocytes, and chondrocytes. Under defined in vitro conditions, MSC have the capacity to differentiate into ectodermal and endodermal-type cellular lineages. In mammals, MSC have been isolated from many tissues sources such as bone marrow, adipose tissue, skin, cardiac muscle, skeletal muscle, umbilical cord blood, liver, lung, nasal septum, synovial membrane, and amniotic membrane.

Several studies have reported protocols to differentiate stem cells into Leydig-like cells (Miyamoto, et al. 2011; Yazawa, et al. 2016; Yazawa, et al. 2011; Yazawa, et al. 2006).

Studies also have reported protocols to differentiate postnatal cells such as fibroblasts into Leydig-like cells (Hou, et al. 2018).

These methods involve stimulation via developmental transcription factors, including the nuclear receptor 5A subfamily (NR5A) proteins—steroidogenic factor-1 (SF-1) and/or liver-specific receptor homologue-1 (LRH-1), GATA4 and/or NGFI-B together with cAMP treatment (Hou et al. 2018; Miyamoto et al. 2011; Yazawa et al. 2016; Yazawa, et al. 2009; Yazawa et al. 2011; Yazawa et al. 2006).

Injection of such cells can increase circulating sex steroid concentrations in rodents (Yang, et al. 2017; Yang, et al. 2015; Yazawa et al. 2016).

Wilms tumor gene, Wt1, is abundantly expressed in testis Sertoli cells. Wt1 is required for the lineage specification of both Sertoli and granulosa cells by repressing Sf1 expression (Chen, et al. 2017). Developmentally, if Wt1 expression is suppressed, the expression of Sf1 drives somatic cells to differentiate into steroidogenic cells instead of supporting cells (Chen et al. 2017). However, SF-1 is essential for Sertoli cell maturation and spermatogenesis, during postnatal testis development (Kato, et al. 2012).

Deletion of the Wt1 results in defects in testosterone biosynthesis, perhaps via a downregulation in the expression of luteinizing hormone receptor (LHR) on Leydig cells and desert hedgehog (Dhh) expression in Sertoli cells (Chen, et al. 2014).

Fetal Leydig cells synthesize only androstenedione as they lack Hsd17b3 expression. Fetal Sertoli cells convert androstenedione to testosterone, whereas adult Leydig cells synthesize testosterone by themselves (Shima, et al. 2013).

SUMMARY OF THE INVENTION

The inventors have discovered compounds that differentiate stem cells into hormone-producing stem cells (FIG. 1). These compounds induce the production of sex steroids, including progesterone, 17β-estradiol, and testosterone.

Namely, the present invention is a method for differentiating stem cells into multiple linages including Leydig-like and Sertoli-like cells (hormone-producing cells), comprising stimulating the stem cells via a NR5A transcription factor and WT-1 expression. Furthermore, said method may comprise further stimulating the MSC by cAMP.

The inventors have discovered cocktails of compounds that result in markedly improved hormone production from stem cells differentiated with these compounds.

The stem cells can be MSCs derived from bone marrow of fat, or induced pluripotent stem cells.

The present invention is a method for producing hormone-producing cells, comprising generating hormone-producing cells by implementing said method in vitro.

Moreover the present invention is for stem cells obtained from humans or other animals.

Embodiments of the present disclosure are capable of utilizing said cells for balancing and maintaining in balance the hypothalamic-pituitary-gonadal (HPG) axis, at least to some extent.

An embodiment of the invention pertains to a method of treating a patient. In this method, a HPG axis of the patient in need thereof is rebalanced by administering a therapeutically effective amount of hormone-producing cells.

Another embodiment of the invention relates to a method of reducing endocrine dyscrasia (dyosis) in a patient. In this method, a HPG axis of the patient in need thereof is rebalanced by administering a therapeutically effective amount of hormone-producing cells.

Yet another embodiment of the invention pertains to a method of reducing rejection in a patient in need of a tissue-specific stem cell transplant. In this method, a HPG axis of the patient in need thereof is rebalanced by administering a therapeutically effective amount of a hormone-producing cell and administering a second stem cell that is tissue-specific to the patient.

Yet another embodiment of the invention relates to a method of preventing or slowing dyosis in a patient. In this method, a therapeutically effective amount of at least one physiological agent that regulates or increases the production of hormones produced by the gonads is administered to a patient.

There has thus been outlined, rather broadly, certain embodiments of the invention in order that the detailed description thereof herein may be better understood, and in order that the present contribution to the art may be better appreciated. There are, of course, additional embodiments of the invention that will be described below and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

ADVANTAGES OF THE PRESENT INVENTION

The present invention provides an improved method for rapidly differentiating stem cells into hormone-producing cells.

The present invention also provides a significant improvement in production of multiple sex hormones from stem cells.

These methods allow for the production of more potent stem cells for transplantation into the gonads of a patient to restore HPG axis balance.

Figure 1:
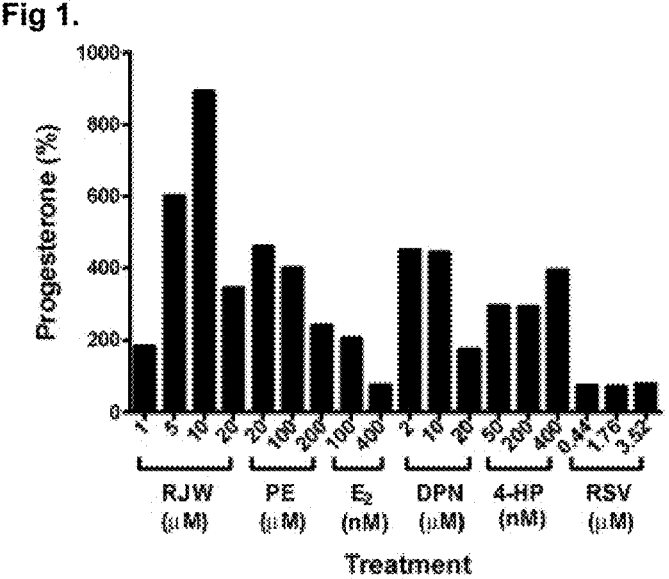
FIG. 1: Treatment of rat MSCs with SF-1 agonists promotes progesterone production. Rat MSC's pre-treated for 7 days with RJW100 (1, 5, 10 or 20 µM); PE (20, 100 or 200 µM); $E_2$ (100 or 400 nM); DPN (2, 10 or 20 µM); 4-HP (50, 200 or 400 nM); RSV (0.44, 1.76 or 3.52 µM), followed by treatment with N6, 2'-O-dibutyryladenosine 3',5'-cyclic monophosphate sodium (dbcAMP) for 3 days, increases progesterone production.
Figure 2:
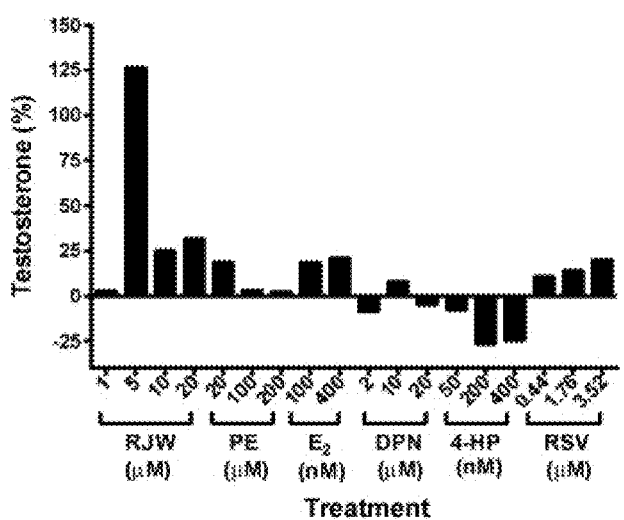
FIG. 2: Treatment of rat MSCs with SF-1 agonists promotes testosterone production. Rat MSC's pre-treated for 7 days with RJW100 (1, 5, 10 or 20 µM); PE (20, 100 or 200 µM); $E_2$ (100 or 400 nM); DPN (2, 10 or 20 µM); 4-HP (50, 200 or 400 nM); RSV (0.44, 1.76 or 3.52 µM), followed by treatment with N6, 2'-O-dibutyryladenosine 3',5'-cyclic monophosphate sodium (dbcAMP) for 3 days, increases testosterone production. No increase was observed for the WT1 inverse agonist 4-HP.
Figure 3:
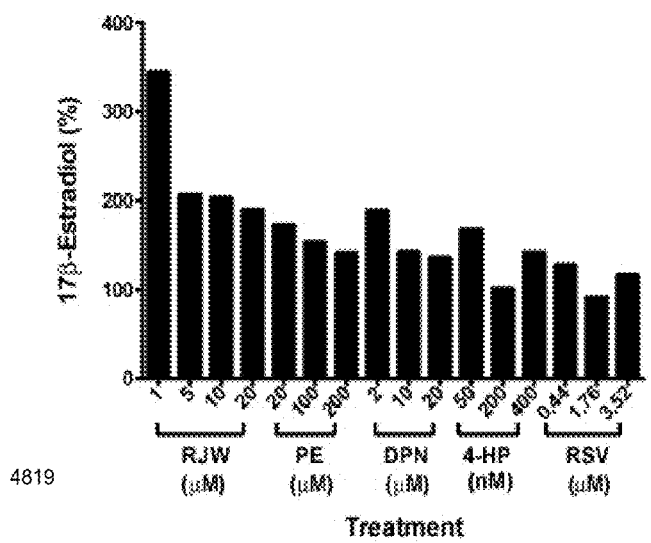
FIG. 3: Treatment of rat MSCs with SF-1 agonists promotes testosterone production. Rat MSC's pre-treated for 7 days with RJW100 (1, 5, 10 or 20 µM); PE (20, 100 or 200 µM); DPN (2, 10 or 20 µM); 4-HP (50, 200 or 400 nM); RSV (0.44, 1,76 or 3.52 µM), followed by treatment with N6, 2'-0-dibutyryladenosine 3',5'-cyclic monophosphate sodium (dbcAMP) for 3 days, increases 17ß-estradiol production.

The drawings presented are intended solely for the purpose of illustration and therefore, are neither desired nor intended to limit the subject matter of the disclosure to any or all of the exact details of construction shown, except insofar as they may be deemed essential to the claims.

DETAILED DESCRIPTION OF THE PREFERRED EMBODIMENTS

The present disclosure relates to a method of differentiating stem and adult cells into hormone-producing cells (or 'steroidogenic cells'; SCs) for use in maintaining in balance or rebalancing, the HPG axis and preventing or reversing hypogonadism and accompanying symptoms and diseases.

The transcriptional factor SF-1 is an inducing factor that is stimulated or blocked by various agonists, inverse agonists and antagonists in the present invention, is an orphan intranuclear receptor, which is expressed in genital and adrenal gland-type steroid hormone-producing cells, and has been known to control the transcription of steroid hormone producing-enzymes (Morohashi and Omura 1996; Parker and Schimmer 1997). Even if SF-1 is derived from different animal species, SF-1 binds to a common target DNA sequence in mesenchymal stem cells and the factor is expected to provide the same result.

The transcriptional factor Wilm's tumor protein (WT-1), is an inducing factor (Barrionuevo, et al. 2012; Chen et al. 2017) that is stimulated or blocked by various agonists, inverse agonists and antagonists in the present invention.

cAMP exists ubiquitously in all living organism, whose intra-cellular concentration is $10^{-6}$ to $10^{-7}$ M. cAMP participates in generation of specific enzymes and metabolic control in target cells and also participates in growth and differentiation of cells. cAMP is a second messenger of luteinizing hormone (LH) and adrenocorticotropic hormone (ACTH), which induces the expression of steroid hormone production-related enzymes in genital and adrenal glands and enhances the production of steroid hormones.

Stimulation of these transcription factors (SF1 and WT1) by cAMP may include the direct contact of these factors with cells or the use of a vector expressing these factors.

To differentiate stem cells into hormone-producing cells, stem cells may be stimulated by an inducing factor in vitro. For example, mesenchymal stem cells may be cultured in a media containing serum or serum components in an incubator with 5% $CO_2$ at 37° C. (see examples).

To differentiate adult cells into hormone-producing cells, adult cells may be stimulated by an inducing factor in vitro. For example, fibroblasts may be cultured in a media containing serum or serum components in an incubator with 5% $CO_2$ at 37° C. (see examples).

The method involves treating stem or adult cells cultured in appropriate medias with one of the following:
1. RJW100 ((Whitby, et al. 2006; Whitby, et al. 2011); LRH-1, SF-1 agonist)
2. Phenylephrine (PE; (Favaretto, et al. 1988; Mayerhofer, et al. 1989); enhances hCG-mediated T secretion, alpha-adrenergic agonist)
3. 17β-Estradiol (E2; (Kumar, et al. 2016); promotes Sertoli cell proliferation)
4. 2,3-Bis(4-hydroxyphenyl)propionitrile ((Royer, et al. 2012; Sato, et al. 2018); DPN)
5. 4-(Heptyloxy)phenol (4-HP; (Del Tredici, et al. 2008); SF-1 inverse agonist)
6. Resveratrol (RSV; (Wu, et al. 2012); SF-1 agonist)
7. Dimethyl sulfoxide (DMSO)

Treatment of stem cells (or iPS cells) individually for 4-7 days with the following compounds at the following concentrations: RJW100 (1 μM, 5 μM, 10 μM, 20 μM); PE (20 μM, 100 μM, 200 μM); E2 (100 nM, 400 nM); DPN (2 μM, 10 μM, 20 μM); 4-HP (50 nM, 200 nM, 400 nM); RSV (0.44, 1.76 or 3.52 μM), followed by treatment with N6, 2'-O-dibutyryladenosine 3',5'-cyclic monophosphate sodium (db-cAMP) for 3 days increases progesterone, testosterone and 17β-estradiol production (FIGS. 1-6).

Figures 4, 5, 6:
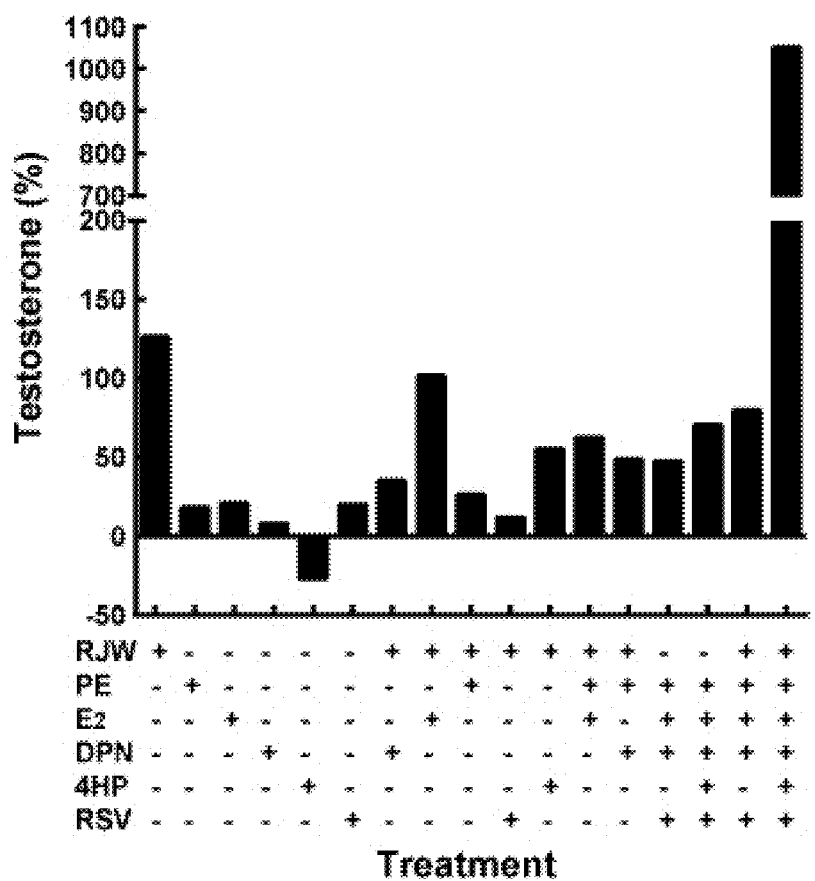
FIG. 4: Treatment of rat MSCs with a combination of SF-1 agonists and the WT-1 inverse agonist dramatically increases testosterone production. Rat MSC's pre-treated for 7 days with 1) RJW100 (5 µM), 2) PE (20 µM), 3); E2 (400 nM), 4) DPN (10 µM), 5) 4-HP (200 nM), or 6) RSV (3.52 µM), or 7) combination of these compounds, followed by treatment with dbcAMP for 3 days, increases testosterone production, with the exception of the WT1 inverse agonist 4-HP alone.
FIG. 5: Treatment of human MSCs with an SF-1 agonist increases testosterone production. Human MSC's pre-treated for 7 days with RJW100 (1, 5 and 10 µM), followed by treatment with dbcAMP for 3 days, increases testosterone production.
FIG. 6: Treatment of human iCell® MSCs (Cellular Dynamics International, Madison, Wis.) with SF-1 agonists and a WT-1 inverse agonist promotes testosterone production. Human iCell® MSCs pre-treated for 7 days with specific combinations of 1) RJW100 (5 µM); 2) PE (20 µM), 3); E2 (400 nM), 4) DPN (10 µM), 5) 4-HP (200 nM), and 6) RSV (3.52 µM), followed by treatment with N6, 2'-O-dibutyryladenosine 3',5'-cyclic monophosphate sodium (dbcAMP) for 3 days, increases testosterone production.

An improved method involves treating stem cells (or iPS cells) cultured in appropriate medias with more than one of the following RJW100 (5 μM), PE (20 μM); E2 (400 nM); DPN (10 μM); 4-HP (200 nM), and RSV (3.52 μM). In particular, the addition of the SF-1 agonist (4-HP), that promotes Sertoli cell differentiation by repressing Sf1 expression (Chen et al., 2017), markedly increases testosterone production from bone-derived MSC and human iCell® MSCs (Cellular Dynamics International, Madison, Wis.; FIGS. 4 and 6).

The presence of Sertoli cells in these cultures provides factors that promote steroid production from neighboring Leydig-like cells.

Figure 7:
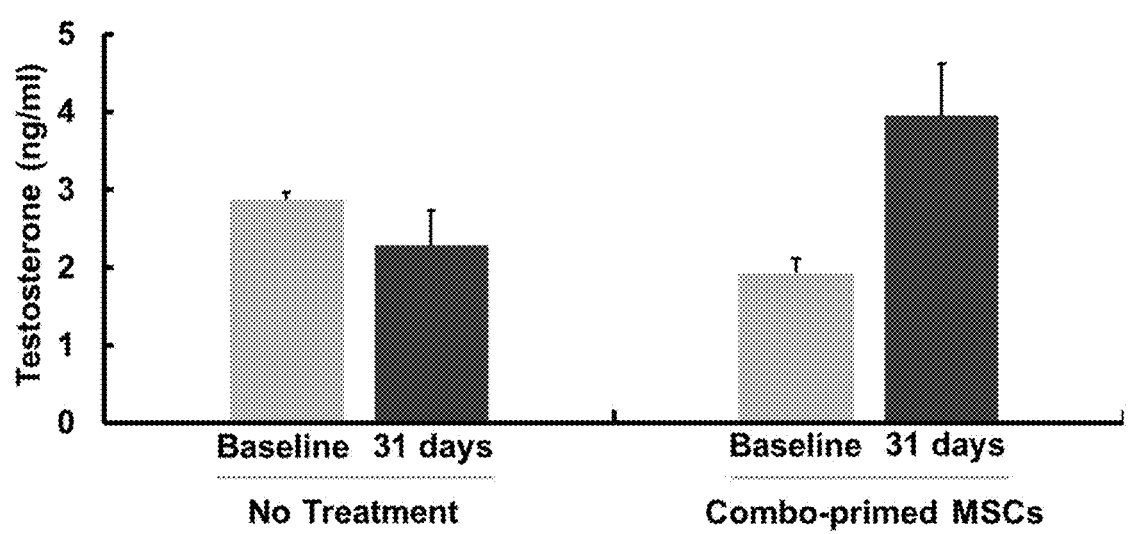
FIG. 7: Injection of educated MSCs into the rat testicle. Rat MSCs pretreated for 7 days with the combination of RJW100 (5 µM), PE (20 µM), $E_2$ (400 nM), DPN (10 µM), 4-HP (200 nM) and RSV (3.52 µM) were injected into the testes (1 million cells/testicle) to increase circulating testosterone concentrations in 8.5 month old male rats.

When this mixture of hormone-producing cells were transplanted into a mammalian reproductive organ, fat pad, or intravenously, there was an increase in circulating testosterone, progesterone and estradiol (FIG. 7).

When hormone-producing cells were transplanted into a mammalian reproductive organ, certain factors activate the cell (endogenous cAMP, LH, FSH) to drive sex hormone production and increased circulating hormone concentrations.

A variation to this method is to inject the transplanted patient with gonadotropin (hCG, LH and/or FSH) at doses sufficient to induce hormone production from the transplanted cells.

When hormone-producing cells were transplanted into a mammalian reproductive organ, certain factors further differentiate the cell (endogenous cAMP, LH, FSH) to become Leydig, Sertoli and other gonadal cells.

Since cAMP is necessarily present in all cells with a large variety of concentrations, intracellular concentration of cAMP will act on transplanted stem cells without adding exogenous cAMP.

Hormone-producing cells derived from stem cells include testicular Leydig cells, testicular Sertoli cells, testicular macrophages, ovarian granulosa cells, ovarian capsular cells, ovarian thecal cells, ovarian macrophages, adrenal cortical cells, and others.

Embodiments of the present invention relates to a method for slowing, preventing or delaying senescence, preventing or treating a disease associated with senescence, and for increasing longevity. This is achieved by delivering donor cells into the human or animal body to increase the production and secretion of sex hormones into the circulation to levels near young adult reproductive levels, thereby reinitiating negative feedback on the hypothalamus and pituitary to rebalance the HPG axis hormone synthesis and secretion to levels near young adult reproductive levels. This in effect prevents dyotic (death) signaling that results from the dysregulation of the HPG axis (Atwood and Bowen 2011; Atwood, et al. 2017; Bowen and Atwood 2004). This will prevent and treat hypogonadism, prevent and treat symptoms associated with female reproductive endocrine dyscrasia and symptoms associated with male reproductive endocrine dyscrasia, and prevent or delay the onset of age-related diseases and extend longevity.

The invention encompasses a method of preventing or reversing the dysregulation of the HPG axis by repopulating the ovaries with follicular cells, and the testes with Leydig, Sertoli and other support cells. This will prevent and treat hypogonadism, prevent and treat symptoms associated with female reproductive endocrine dyscrasia and symptoms associated with male reproductive endocrine dyscrasia, and prevent and delay the onset of age-related diseases and extend longevity.

The invention encompasses a method of restoring the HPG axis to balance (young adult reproductive levels) by repopulating the ovaries with follicular cells, and the testes with Leydig, Sertoli and other support cells. This will reverse hypogonadism, prevent and treat symptoms associated with female reproductive endocrine dyscrasia and symptoms associated with male reproductive endocrine dyscrasia, and prevent and delay the onset of age-related diseases and extend longevity.

The invention further encompasses a method of inhibiting inflammation such as decreasing the expression of tumor necrosis factor (TNF), in a subject, by administering donor cells that lead to a rebalancing of the HPG axis.

Thus, the present invention encompasses reversing the degenerative serum hormonal milieu back to one that allows the appropriate growth and development of cells for the normal maintenance of tissue structure and function in the body. Rebalancing the endocrine HPG axis will allow for the rebalancing of the tissue specific 'mini-HPG' axes present in tissues throughout the body (Meethal et al. 2009b). This will rebalance reproductive hormone signaling to cells in all tissues of the body.

The present invention encompasses a method of maintaining HPG axis hormones in balance to extend longevity for purposes of extending longevity of animals with agricultural applications, such as increasing yields of wool, cashmere or other fibers per animal. Similar applications apply to egg and milk production.

This can be achieved by injecting into a subject donor cells that can repopulate the gonads with cell types capable of producing reproductive hormones required to balance the HPG axis. For male subject, donor cells capable of differentiating into germ cells (spermatogonia, spermatocytes, spermatids and spermatozoon), Sertoli cells, myoid cells, Leydig cells, stromal cells, macrophage cells and/or epithelial cells and integrating into the tissue to restore function. For female subject, donor cells capable of differentiating into germ cells (oogonial stem cells), granulosa cells, cumulus cells, thecal cells, stromal cells, epithelial cells, macrophage cells and/or oocyte cells, and integrating into the tissue to restore function.

The differentiation of donor cells into more than one gonadal cell type is required to allow complete rebalancing of the axis. For example, while Leydig cells primarily produce androgens, Sertoli cells produce large quantities of inhibins, both of which are required for HPG axis rebalancing in males. A combination of gonadal cells is optimal for complete rebalancing of the axis.

An embodiment of the present invention includes administering, to a subject, donor cells that decrease or regulate the blood levels, production, function or activity of gonadal hormone to be near the blood levels, production, function or activity occurring during fetal life or at or around the height of the subject's reproductive period, which in humans usually corresponds to about 18 to 35 years of age.

In another embodiment, the present invention encompasses administering, to a subject, donor cells that decrease or regulate the blood levels, production, function or activity of kisspeptin, GnRH, LH or FSH to be approximately as low as possible without significant adverse side effects, preferably to be undetectable or nearly undetectable by conventional detection techniques known in the art, which, at the present time, is less than 0.7 mIU/mL for both LH and FSH. In another embodiment, the present invention encompasses administering, to a subject, donor cells that regulate the function or activity of activin to be approximately as low as possible without significant adverse side effects, preferably to be undetectable or nearly undetectable by conventional detection techniques known in the art. In another embodiment, the present invention encompasses administering donor cells that increase or regulate the blood levels, production, function, or activity of inhibin, follistatin, myostatin or BMP4 to be approximately as high as possible without significant adverse side effects.

In other embodiments of the present invention, the blood levels, production, function or activity of gonadal hormones are continuously regulated, by monitoring the blood levels, production, function or activity and making adjustments to the donor cell or donor cells being administered via a feedback control system.

Embodiments of the present invention include administration of one or more stem or differentiated cell types that can be used to increase or regulate the blood and/or tissue levels, production, function or activity of gonadal hormones. Studies have shown that increasing the levels of circulating sex steroids and inhibins will result in significant decreases in GnRH, LH and FSH levels and a rebalancing of the HPG axis (Hayes, et al. 1998; Thorner et al. 1998; Ying 1988). Through a negative feedback loop, the presence of sex steroid hormones such as estrogen, testosterone or progesterone signals the hypothalamus to decrease the secretion of GnRH (Gharib, et al. 1990; Steiner, et al. 1982). The subsequent decrease in GnRH decreases the secretion of LH and FSH (Thorner et al. 1998). For example, sex steroids, inhibins and follistatin have been shown to provide negative feedback regulation of GnRH and FSH synthesis and secretion (Bagatell, et al. 1994; Boepple, et al. 2008; Dubey, et al. 1987; Hayes, et al. 2001b; Illingworth, et al. 1996; Lambert-Messerlian, et al. 1994; Marynick, et al. 1979; Pitteloud, et al. 2008a, b; Schnorr, et al. 2001; Sherins and Loriaux 1973; Winters, et al. 1979a; Winters, et al. 1979b) while sex steroids appear to primarily provide negative feedback for the regulation of GnRH and LH synthesis and secretion (Bagatell et al. 1994; Hayes, et al. 2001a; Santen 1975; Schnorr et al. 2001; Veldhuis, et al. 1992). In females, sex steroids, inhibins and follistatin have been shown to provide negative feedback regulation of FSH (le Nestour, et al. 1993; Welt, et al. 1997) and LH (Jaffe and Keye 1974, 1975; Jaffe, et al. 1976; Keye and Jaffe 1974, 1975, 1976; Liu and Yen 1983; Taylor, et al. 1995; Young and Jaffe 1976) synthesis and secretion.

Embodiments of the present invention also encompass rebalancing of the HPG axis such that the axis and related hormonal concentrations are balanced for that person. The production of sex hormones by donor cells is expected to be different for different individuals in order to reach optimal balancing of that person's HPG axis. Thus, the circulating and tissue concentrations of sex hormones in one person's balanced HPG axis is expected to be different to that of another person whose axis is also balanced.

Embodiments of the present invention also encompass the minute-to-minute, hour-to-hour and day-to-day variations in HPG axis hormone production to allow the axis to remain in balance.

Embodiments of the present invention also encompass modulating the concentrations and ratios of hormones of the HPG axis at any stage of the life cycle, including the embryo, fetus, childhood, puberty, adulthood or during senescence.

Embodiments of the present invention also encompass modulating the concentrations and ratios of hormones of the HPG axis during gender transition from male to female, or female to male.

Embodiments of the present invention also encompass returning the ratios of sex hormones back to near the ratios occurring during fetal life or at or near the time of greatest reproductive function of the subject. For example, the ratio of testosterone:FSH during the male reproductive period is ~11 (6.5 ng/mL:0.6 ng/mL), while that during the post-reproductive period (post-menopause) is ~1 (2.3 ng/mL:2.3 ng/mL). In this example, treatment would aim to return the ratio of these hormones back to 11. Further embodiments to this invention would encompass returning all the sex hormone ratios back to those during fetal life or at the time of greatest reproductive function of the subject.

Embodiments of the present invention also encompass administration of purified and mixed donor cell populations derived from the tissues of an individual who will receive the donor cells.

Embodiments of the present invention also encompass administration to an individual purified and mixed donor cell populations derived from multiple tissues of one or more individuals.

Embodiments of the present invention encompass administration of autologous or allogenic donor cell populations into the gonads for the prevention or treatment of hypogonadism, hypergonadotropic hypogonadism, andropause, menopause and related conditions, and for the prevention and treatment of diseases associated with senescence and aging.

Embodiments of the present invention also encompass administration of donor cell populations into the gonads prior to administration of donor cell populations (e.g. stem cell therapy, iPS therapy, or implantation/injection of differentiated cells including stem cells that have been differentiated in vitro) into other tissues of the body. Such a method allows for rebalancing the HPG axis so that the 'toxic environment of dyotic signaling' is reversed in order to allow for donor cells transplanted into other tissues to differentiate appropriately, integrate into the tissue and restore function.

In other embodiments of the invention, donor cell recipients may receive supplemental gonadal hormones, GnRH agonists/antagonists, an LH/FSH-inhibiting agent, an activin-inhibiting agent, an inhibin-promoting agent, and/or a follistatin-promoting agent.

According to embodiments of the present invention, administration of GnRH agonists/antagonists, LH/FSH-inhibiting agents, activin-inhibiting-agents, inhibin-promoting agents, follistatin-promoting agents, or sex steroids, including those listed above, can be oral or by injection, inhalation, patch, or other effective means. According to embodiments of the present invention, the dosage of GnRH agonists/antagonists, LH/FSH-inhibiting agents, activin-inhibiting agents, inhibin-promoting agents, follistatin-promoting agents, or sex steroids, including those identified above, will be a therapeutically effective amount, sufficient to decrease or regulate the blood and/or tissue levels, production, function or activity of GnRH, LH or FSH, or to decrease or regulate the function or activity of activin or to increase or regulate the blood and/or tissue levels, production, function or activity of inhibin or follistatin, to the desired blood and/or tissue levels, production, function or activity. According to other embodiments of the invention, administration of LH/FSH-inhibiting agents, activin-inhibiting agents, inhibin-promoting agents, follistatin-promoting agents, or sex steroids, including those identified above, can be in a single dose, multiple doses, in a sustained release dosage form, in a pulsatile form, or in any other appropriate dosage form or amount. Administration prior to treatment with cells is preferred, but can occur during or after administration of cells. The duration of treatment could range from a few days or weeks to the remainder of the patient's life.

In addition to treating neurodegenerative diseases, the administration of GnRH agonists/antagonists, LH/FSH-inhibiting agents, activin-inhibiting agents, inhibin-promoting agents, follistatin-promoting agents, sex steroids, or other agents that decrease dysregulated cell cycle signaling, as described above, is expected to be beneficial as a prophylactic or in the treatment of aging and diseases where cell replenishment is required in order to repopulate a tissue to regain function or establish a new function, in accordance with the present invention.

EXAMPLES

Example 1

General Overview of Stem Cell Education into Hormone-Producing Stem Cells

Adult stem mesenchymal stem cells (MSCs) (or bone marrow stromal cells), are pluripotent cells that have the ability to differentiate into cells of all three germ layers (Ratajczak, et al. 2008).

In the case of a human male or female, MSCs are isolated from 1) bone, the femur and/or tibia (Tuli, et al. 2003a; Tuli, et al. 2003b), 2) umbilical cord blood (Hayward, et al. 2013; Malgieri, et al. 2010), 3) Wharton's jelly (Hayward et al. 2013), 4) skin (Manini, et al. 2011) or 5) adipose tissue (Kuhbier, et al. 2010; Manini et al. 2011; Tholpady, et al. 2003; Zhu, et al. 2013; Zuk, et al. 2001). Cells are then subjected to flow cytometry to isolate MSC that are then injected (10,000-1 billion cells/treatment) into the interstitium of one or both testes or ovaries of the donor. In the testes, cells can be injected into the seminal vesicle lobules, septa, tunica albuginea, straight tubule, rete testes, efferent ductile and/or epididymis. In the ovary, cells can be injected into the ovarian cortex. If the number of isolated MSCs is insufficient, MSCs are expanded in culture first prior to injection into the gonads.

Stem cells and educated stem cells (e.g. MSCs differentiated into hormone-producing stem cells) injected into the testes localize to the testicular interstitium and seminiferous tubules and differentiate into Leydig cells and spermatogonia/spermatocytes, respectively (Lo, et al. 2004; Yazawa et al. 2006). Stem cells injected into the ovaries increase follicle numbers (Abd-Allah, et al. 2013). Hormonal factors secreted within the gonads direct the differentiation and integration of such stem cells for the replenishment of germ cells, Leydig, Sertoli and other cells in the testes, and replenishment of follicular cells (germ cells, granulosa, thecal and other cells) in the ovaries. Hormones secreted by the transplanted cells and their progeny in turn rebalance the HPG axis.

This technique may be performed autologously, i.e. isolating cells from the same individual who will receive the cells; allogeneically, i.e. cells isolated from one individual are injected into another individual (human or animal); or both autologously and allogeneically, i.e. isolated cells from the recipient and from another individual(s) are injected into the recipient.

In this example, MCSs, from which gonadal tissues are derived during embryogenesis, are purified from tissues other than the gonads and then injected into the gonads.

MSCs in a suitable buffer, or encapsulated in a hydrogel or other matrix (e.g. fibrin, collagen) prior to injection, may be injected into the gonads (testes or ovaries). Injection may be via a catheter. MSCs in this example are capable of differentiating into all relevant gonadal cell types upon injection into the gonads.

This technique can be used on humans, animals and plants with a reproductive hormone axis.

Following transplantation of cells, the patient can be treated with gonadotropins (hCG, LH and/or FSH) to induce further differentiation hormone production.

The concentration of circulating reproductive hormones in the individual can be measured before and after the injection of cells to confirm that injected cells are producing hormones and rebalancing the HPG axis. Tissue concentrations of reproductive hormones can be measured in tissues to confirm that the hormones of the 'mini-HPG-axis in that tissue have rebalanced (returned to young adult reproductive concentrations). If the HPG axis has not completely rebalanced, a second or subsequent injection can be given until such time as the HPG axis is balanced and dyotic signaling has decreased. This provides a preventative and treatment for hypogonadism (primary) and of age-related reproductive endocrine dyscrasia.

Example 2

MSC Education into Hormone-Producing Cells

MSCs or other stem cell populations are differentiated in vitro into discrete precursor or differentiated cell types including germ cells (spermatogonia, spermatocytes, spermatids and spermatozoon), Sertoli cells, myoid cells, Leydig cells, stromal cells, macrophage cells and/or epithelial cells in the case of the male; or germ cells (oogonial stem cells), granulosa cells, cumulus cells, thecal cells, stromal cells, epithelial cells, macrophage cells and/or oocyte cells, in the case of the female, and one or preferably more of these cell types are injected into the gonads and/or other tissues and circulating and tissue sex hormone concentrations measured as in the methods described in Example 1, for rebalancing of the HPG axis.

Bone marrow derived hMSC are grown to confluence in T75 flasks using Minimum Essential Medium (MEM)—Alpha 1, with Earle's salts, Glutagro Supplement, L-alanyl-L-glutamine, MEM nonessential amino acids and HyClone fetal bovine serum prior to treatment with differentiation factors.

MSCs are differentiated into hormone-producing cells over 7-21 days in a water-jacketed $CO_2$ incubator (Thermo Electron Corporation, Waltham, Mass.) at 37° C. with 5% $CO_2$ by treatment with RJW100 (5 µM), PE (20 µM); $E_2$ (400 nM); DPN (10 µM); 4-HP (200 nM), and RSV (3.52 µM).

Hormone production can be induced in educated cells by treatment with N6, 2'-O-dibutyryladenosine 3',5'-cyclic monophosphate sodium (dbcAMP), or following treatment with LH, FSH and/or hCG, for 1-3 days in serum supplement-free media.

Sex steroid and protein hormone concentrations are measured in the media.

Cells are then injected into a patient, including the gonads or fat pad, and the patient can be treated with gonadotropins (LH, FSH and/or hCG) to aid in repopulation, cell differentiation and hormone production.

Example 3

Induced pluripotent stem (iPS) cells created from the recipient or another donor can be cultured to produce sufficient cell numbers to be injected into either one or both of the gonads, and/or injected into the circulation, and/or other tissues of the body and circulating and tissue sex hormone concentrations measured as described in Example 1 to rebalance the HPG axis. Differentiated cells such as fibroblasts, umbilical cord fibroblasts stomach, hepatocytes, lymphocytes, prostatic cells and other adult differentiated cells can be obtained by various techniques known in the field and reprogrammed into iPS cells via the following techniques also known in the field.

Human iCell® Mesenchymal Stem Cells (iCell MSC; Cellular Dynamics International, Madison, Wis.) are grown to confluence in iCell maintenance media that includes L-Ascorbic Acid, B-27 supplement minus vitamin A, recombinant human FGF-basic, bovine serum albumin, GlutaMAX supplement, Ham's F-12 medium, Iscove's Modified Dulbecco's Medium, 1-Thioglycerol, N-2 supplement, recombinant human PDGF-BB, and penicillin/streptomycin. The iCell MSC are differentiated into hormone-producing cells over 7-21 days in a water-jacketed $CO_2$ incubator (Thermo Electron Corporation, Waltham, Mass.) at 37° C. with 5% $CO_2$ by treatment with RJW100 (5 µM), PE (20 µM); $E_2$ (400 nM); DPN (10 µM); 4-HP (200 nM), and RSV (3.52 µM).

Hormone production can be induced in educated cells by treatment with N6, 2'-O-dibutyryladenosine 3',5'-cyclic monophosphate sodium (dbcAMP), or following treatment with LH, FSH and/or hCG, for 1-3 days in serum supplement-free media.

Sex steroid and protein hormone concentrations are measured in the media.

Cells can be administered to patients as described in the examples above and below.

Example 4

The above techniques can also be used to differentiate post-natal fibroblasts from foreskin or punch biopsies into Leydig-like and Sertoli-like cells.

Example 5

Adult testicular cells such as Leydig cells, Sertoli cells, and germ cells can be differentiated from MSCs following transfection with members of the nuclear receptor family, SF-1, liver receptor homolog-1 (LRH-1), and/or Wilms tumor protein (WT1), and treatment with 8-bromoadenosine-cAMP ((Yazawa et al. 2006); WT1). One or preferably both of these cell types are injected into the male gonads and/or other tissues neat or in matrices via methods described in Example 1 and circulating and tissue sex hormone concentrations measured as in the methods described in Example 1, for rebalancing of the HPG axis. Cells may be autologous or allogeneic. In a derivation of this method, MSC or other cell types are treated with differentiation factors as described in Example 3, and injected within 24 h into the testes via methods described in Example 1. In another derivation of this method, MSC or other cell types are imbedded in a matrix impregnated with differentiation factors and injected into the testes via methods described in Example 1.

Generation of iPSCs

Reprogramming With Lentiviral Transduction

Three plasmid vectors of lentiviral reprogramming: FUW-tetO-lox-hO2S, FUW-tetO-lox-hM2K, and FUW-tetO-lox-hN2L are constructed. Expression cassettes of human POU5F1-internal ribosome entry site 2 (IRES2)-SOX2 (O2S) and MYC-IRES2-KLF4 (M2K) of pEP4 EO2S EM2K (Addgene, #20923) (Yu, et al. 2009) are used for the O2S and M2K cassettes. Pseudovirus is produced in 293FT cells by transfection with each lentiviral vector (O2S, M2K, N2L) and the reverse tetracycline transactivator expression plasmid, FUW-M2rtTA (Addgene, plasmid 20342) (Hockemeyer, et al. 2008) along with the VSV-G envelope (pMD2.G) and packaging vector (psPAX2) (Ezashi, et al. 2009). Two consecutive infections are introduced into the target cell or interest ($1\times10^5$ cells) in the presence of 12 µg/ml hexadimethrine bromide (polybrene, Sigma, St. Louis, Mo.). During the infection stage, the cells are cultured for 48 h by adding a mixture of the four titered pseudoviruses (multiplicity of infection); O2S (30.8), M2K (17.5), N2L (18.2) and rtTA (20.7) to the culture medium. On day 4 after infection, cells are dispersed with trypsin and then expanded. Cells are tested for pluripotency and can then be used for treatment.

Reprogramming With Episomal Plasmids

Episomal vectors carrying the reprogramming genes SOX2, KLF4, POU5F1, LIN28, p53 and MYCL (combined episomal plasmids; Addgene #27077, 27078 and 27080) are electroporated into $1-6\times10^5$ cells using a Nucleofector II device (Lonza, Basel, Switzerland) and Amaxa NHDF Nucleofector kit (Lonza). After 20 days, colonies resembling human ESC are mechanically isolated and expanded in mTeSR1 medium (Gallego, et al. 2010; Ludwig, et al. 2006; Porayette, et al. 2009) (StemCell Technologies, Vancouver, Canada) on a Matrigel (BD Bioscience, San Jose, Calif.) coated substratum. Cells are tested for pluripotency and can then be used for treatment.

Example 6

Adult granulosa, cumulus, thecal and germ cells can be isolated from adult ovaries following tituration, percoll gradients and/or flow cytometry (Sittadjody, et al. 2013) and one or preferably more of these cell types, educated cell types, or bioengineered cell types as described in the above examples injected into the female gonads and/or other tissues and circulating and tissue sex hormone concentrations measured as in the methods described in Examples 1-4, for rebalancing of the HPG axis.

Example 7

This Technique Can be Used on Humans, Animals and Plants with a Reproductive Hormone Axis Example 8

The patient is pre-treated with agents to lower dyotic signaling, such as GnRH agonists/antagonists and/or sex steroid supplementation (e.g. testosterone in males; estradiol and progesterone in females), prior to treatment with donor cells as outlined in Examples 1-7 to aid in the repopulation of gonadal cells.

Pre-treatment of patients described above is performed prior to the injection of donor cells into non-gonadal tissues or the circulation, and tissue regeneration and function monitored.

Example 9

The above methods in Examples 1-8 can be utilized to rebalance the HPG axis and reverse or prevent dyotic signaling in tissues, thereby allowing for a more conducive environment for innate tissue regeneration or regeneration aided by treatment with donor cells. The methods from Examples 1-8 can be performed on patients, circulating and tissue sex hormone concentrations measured to confirm the HPG axis is rebalanced and that dyotic signaling has decreased, prior to the injection of donor cells into specific tissues or the circulation, and tissue regeneration and function monitored. As one example, the method of Example 1 can be used to decrease dyotic signaling to the brain, and donor cells (e.g. neural stem cells, iPS cells or differentiated neural cells) injected into a dysfunctioning region(s) of the brain.

Example 10

These techniques can be used to treat hypogonadotropic hypogonadism (secondary hypogonadism), a condition characterized by hypogonadism due to an impaired secretion of gonadotropins, including FSH and LH, by the pituitary gland in the brain, and in turn decreased gonadotropin levels and a resultant lack of sex steroid production. Pituitary cell types such as gonadotrophs, corticotrophs, thyrotrophs, lactotrophs and adipose generated by way of Examples 1-3, 5-7, and from pituitary tissue, can be cultured to produce sufficient cell numbers to be injected into the pituitary, and/or injected into the circulation, and/or other tissues of the body to rebalance the HPG axis as described in Examples 1-8 with or without pre-treatment of patients described in Example 8. Circulating and tissue sex hormone concentrations measured as described in Example 1 are performed to confirm rebalancing of the HPG axis. Conditions and diseases treated by this method include secondary congenital forms of hypogonadism (hypogonadotropic hypogonadism): Kallman syndrome, isolated GnRH deficiency, isolated LH deficiency, Prader-Willi syndrome, Turner syndrome, and Laurence-Moon-Biedl syndrome; and secondary acquired forms of hypogonadism: pituitary tumors and infarct, trauma, mumps, traumatic brain injury, children born to mothers who had ingested the endocrine disruptor diethylstilbestrol, opioid induced androgen deficiency (resulting from the prolonged use of opioid class drugs, e.g. morphine, oxycodone, methadone, fentanyl, hydromorphone), anabolic steroid-induced hypogonadism craniopharyngioma, hyperprolactemia (1° & 2°), hemochromatosis and neurosarcoid.

Example 11

The above techniques also can be used to treat other dysregulated hormone axes of the body, including conditions and diseases that dysregulate the hypothalamic-pituitary-adrenal axis (e.g. adrenal insufficiency, Cushing's syndrome, Addison disease), alimentary system hormone axes, placental hormone axes, calcium regulatory axes, salt regulatory axes, thermoregulatory axes and thyroid hormone axes Example 12

The above techniques in Examples 1-12 can be used to treat animals such as stud bulls or horses, pets and members of rare and endangered species in order to restore hormone balance and improve or maintain health and lifespan.

CONCLUSION

While various embodiments of the present invention have been described above, it should be understood that they have been presented by way of example only, and not by limitation. For example, the present invention is not limited to the stem or differentiated cells illustrated or described, the methods of injection, the hormones produced by the cells, or the injected tissues illustrated or described. In another example, although some cells and techniques described herein are related to humans, the present invention is not limited to humans, but rather, includes all reproductively viable organisms. As such, the breadth and scope of the present invention should not be limited to any of the above-described exemplary embodiments, but should be defined only in accordance with the following claims and their equivalents.

REFERENCES

Abd-Allah S H, Shalaby S M, Pasha H F, El-Shal A S, Raafat N, Shabrawy S M, Awad H A, Amer M G, Gharib M A, El Gendy E A, et al. 2013 Mechanistic action of mesenchymal stem cell injection in the treatment of chemically induced ovarian failure in rabbits. *Cytotherapy* 15 64-75.

Atwood C S & Bowen R L 2011 The reproductive-cell cycle theory of aging: an update. *Experimental Gerontology* 46 100-107.

Atwood C S, Hayashi K, Meethal S V, Gonzales T & Bowen R L 2017 Does the degree of endocrine dyscrasia post-reproduction dictate post-reproductive lifespan? Lessons from semelparous and iteroparous species. *GeroScience* 39 103-116.

Barrionuevo F J, Burgos M, Scherer G & Jimenez R 2012 Genes promoting and disturbing testis development. *Histology and histopathology* 27 1361-1383.

Bowen R L & Atwood C S 2004 Living and dying for sex. A theory of aging based on the modulation of cell cycle signaling by reproductive hormones. *Gerontology* 50 265-290.

Chen M, Wang X, Wang Y, Zhang L, Xu B, Lv L, Cui X, Li W & Gao F 2014 Wt1 is involved in leydig cell steroid hormone biosynthesis by regulating paracrine factor expression in mice. *Biology of Reproduction* 90 71.

Chen M, Zhang L, Cui X, Lin X, Li Y, Wang Y, Qin Y, Chen D, Han C, Zhou B, et al. 2017 Wt1 directs the lineage specification of sertoli and granulosa cells by repressing Sf1 expression. *Development* 144 44-53.

Del Tredici A L, Andersen C B, Currier E A, Ohrmund S R, Fairbain L C, Lund B W, Nash N, Olsson R & Piu F 2008 Identification of the first synthetic steroidogenic factor 1 inverse agonists: pharmacological modulation of steroidogenic enzymes. *Molecular pharmacology* 73 900-908.

Ezashi T, Telugu B P, Alexenko A P, Sachdev S, Sinha S & Roberts R M 2009 Derivation of induced pluripotent stem cells from pig somatic cells. *Proceedings of the National Academy of Sciences of the United States of America* 106 10993-10998.

Favaretto A L, Valenca M M, Hattori M, Wakabayashi K & Antunes-Rodrigues J 1988 Characterization of adrenergic control of the Leydig cell steroidogenesis: identification of both stimulatory and inhibitory components. *Brazilian journal of medical and biological research=Revista brasileira de pesquisas medicas e biologicas* 21 539-543.

Gallego M J, Porayette P, Kaltcheva M M, Bowen R L, Vadakkadath Meethal S & Atwood C S 2010 The pregnancy hormones human chorionic gonadotropin and progesterone induce human embryonic stem cell proliferation and differentiation into neuroectodermal rosettes. *Stem cell research & therapy* 1 28.

Hayward C J, Fradette J, Galbraith T, Remy M, Guignard R, Gauvin R, Germain L & Auger F A 2013 Harvesting the potential of the human umbilical cord: isolation and characterisation of four cell types for tissue engineering applications. *Cells, tissues, organs* 197 37-54.

Hockemeyer D, Soldner F, Cook E G, Gao Q, Mitalipova M & Jaenisch R 2008 A drug-inducible system for direct reprogramming of human somatic cells to pluripotency. *Cell stem cell* 3 346-353.

Hou Y P, Zhang Z Y, Xing X Y, Zhou J & Sun J 2018 Direct conversion of human fibroblasts into functional Leydig-like cells by SF-1, GATA4 and NGFI-B. *American journal of translational research* 10 175-183.

Kato T, Esaki M, Matsuzawa A & Ikeda Y 2012 NR5A1 is required for functional maturation of Sertoli cells during postnatal development. *Reproduction* 143 663-672.

Kuhbier J W, Weyand B, Radtke C, Vogt P M, Kasper C & Reimers K 2010 Isolation, characterization, differentiation, and application of adipose-derived stem cells. *Advances in biochemical engineering/biotechnology* 123 55-105.

Kumar N, Srivastava S, Burek M, Forster C Y & Roy P 2016 Assessment of estradiol-induced gene regulation and proliferation in an immortalized mouse immature Sertoli cell line. *Life sciences* 148 268-278.

Lo K C, Lei Z, Rao Ch V, Beck J & Lamb D J 2004 De novo testosterone production in luteinizing hormone receptor knockout mice after transplantation of leydig stem cells. *Endocrinology* 145 4011-4015.

Ludwig T E, Bergendahl V, Levenstein M E, Yu J, Probasco M D & Thomson J A 2006 Feeder-independent culture of human embryonic stem cells. *Nature methods* 3 637-646.

Malgieri A, Kantzari E, Patrizi M P & Gambardella S 2010 Bone marrow and umbilical cord blood human mesenchymal stem cells: state of the art. *International journal of clinical and experimental medicine* 3 248-269.

Manini I, Gulino L, Gava B, Pierantozzi E, Curina C, Rossi D, Brafa A, D'Aniello C & Sorrentino V 2011 Multi-potent progenitors in freshly isolated and cultured human mesenchymal stem cells: a comparison between adipose and dermal tissue. *Cell and tissue research* 344 85-95.

Mayerhofer A, Bartke A & Steger R W 1989 Catecholamine effects on testicular testosterone production in the gonadally active and the gonadally regressed adult golden hamster. *Biology of Reproduction* 40 752-761.

Miyamoto K, Yazawa T, Mizutani T, Imamichi Y, Kawabe S Y, Kanno M, Matsumura T, Ju Y & Umezawa A 2011 Stem cell differentiation into steroidogenic cell lineages by NR5A family. *Molecular and cellular endocrinology* 336 123-126.

Morohashi K I & Omura T 1996 Ad4BP/SF-1, a transcription factor essential for the transcription of steroidogenic cytochrome P450 genes and for the establishment of the reproductive function. *FASEB journal: official publication of the Federation of American Societies for Experimental Biology* 10 1569-1577.

Parker K L & Schimmer B P 1997 Steroidogenic factor 1: a key determinant of endocrine development and function. *Endocrine reviews* 18 361-377.

Porayette P, Gallego M J, Kaltcheva M M, Bowen R L, Vadakkadath Meethal S & Atwood C S 2009 Differential processing of amyloid-beta precursor protein directs human embryonic stem cell proliferation and differentiation into neuronal precursor cells. *The Journal of biological chemistry* 284 23806-23817.

Royer C, Lucas T F, Lazari M F & Porto C S 2012 17Beta-estradiol signaling and regulation of proliferation and apoptosis of rat Sertoli cells. *Biology of Reproduction* 86 108.

Sato T, Kim H, Kakuta H & Iguchi T 2018 Effects of 2,3-Bis(4-hydroxyphenyl)-propionitrile on Induction of Polyovular Follicles in the Mouse Ovary. *In vivo* 32 19-24.

Shima Y, Miyabayashi K, Haraguchi S, Arakawa T, Otake H, Baba T, Matsuzaki S, Shishido Y, Akiyama H, Tachibana T, et al. 2013 Contribution of Leydig and Sertoli cells to testosterone production in mouse fetal testes. *Molecular endocrinology* 27 63-73.

Sittadjody S, Saul J M, Joo S, Yoo J J, Atala A & Opara E C 2013 Engineered multilayer ovarian tissue that secretes sex steroids and peptide hormones in response to gonadotropins. *Biomaterials* 34 2412-2420.

Tholpady S S, Katz A J & Ogle R C 2003 Mesenchymal stem cells from rat visceral fat exhibit multipotential differentiation in vitro. *The anatomical record. Part A, Discoveries in molecular, cellular, and evolutionary biology* 272 398-402.

Tuli R, Seghatoleslami M R, Tuli S, Wang M L, Hozack W J, Manner P A, Danielson KG & Tuan RS 2003a A simple, high-yield method for obtaining multipotential mesenchymal progenitor cells from trabecular bone. *Molecular biotechnology* 23 37-49.

Tuli R, Tuli S, Nandi S, Wang M L, Alexander P G, Haleem-Smith H, Hozack W J, Manner P A, Danielson K G & Tuan R S 2003b Characterization of multipotential mesenchymal progenitor cells derived from human trabecular bone. *Stem Cells* 21 681-693.

Whitby R J, Dixon S, Maloney P R, Delerive P, Goodwin B J, Parks D J & Willson T M 2006 Identification of small molecule agonists of the orphan nuclear receptors liver receptor homolog-1 and steroidogenic factor-1. *Journal of medicinal chemistry* 49 6652-6655.

Whitby R J, Stec J, Blind R D, Dixon S, Leesnitzer L M, Orband-Miller L A, Williams S P, Willson T M, Xu R, Zuercher W J, et al. 2011 Small molecule agonists of the orphan nuclear receptors steroidogenic factor-1 (SF-1, NR5A1) and liver receptor homologue-1 (LRH-1, NR5A2). *Journal of medicinal chemistry* 54 2266-2281.

Wu L, Zhang A, Sun Y, Zhu X, Fan W, Lu X, Yang Q & Feng Y 2012 Sirt1 exerts anti-inflammatory effects and promotes steroidogenesis in Leydig cells. *Fertility and Sterility* 98 194-199.

Yang Y, Li Z, Wu X, Chen H, Xu W, Xiang Q, Zhang Q, Chen J, Ge RS, Su Z, et al. 2017 Direct Reprogramming of Mouse Fibroblasts toward Leydig-like Cells by Defined Factors. *Stem cell reports* 8 39-53.

Yang Y, Su Z, Xu W, Luo J, Liang R, Xiang Q, Zhang Q, Ge R S & Huang Y 2015 Directed mouse embryonic stem cells into leydig-like cells rescue testosterone-deficient male rats in vivo. *Stem cells and development* 24 459-470.

Yazawa T, Imamichi Y, Miyamoto K, Khan M R, Uwada J, Umezawa A & Taniguchi T 2016 Induction of steroidogenic cells from adult stem cells and pluripotent stem cells [Review]. *Endocrine journal* 63 943-951.

Yazawa T, Inanoka Y, Mizutani T, Kuribayashi M, Umezawa A & Miyamoto K 2009 Liver receptor homolog-1 regulates the transcription of steroidogenic enzymes and induces the differentiation of mesenchymal stem cells into steroidogenic cells. *Endocrinology* 150 3885-3893.

Yazawa T, Kawabe S, Inaoka Y, Okada R, Mizutani T, Imamichi Y, Ju Y, Yamazaki Y, Usami Y, Kuribayashi M, et al. 2011 Differentiation of mesenchymal stem cells and embryonic stem cells into steroidogenic cells using steroidogenic factor-1 and liver receptor homolog-1. *Molecular and cellular endocrinology* 336 127-132.

Yazawa T, Mizutani T, Yamada K, Kawata H, Sekiguchi T, Yoshino M, Kajitani T, Shou Z, Umezawa A & Miyamoto K 2006 Differentiation of adult stem cells derived from bone marrow stroma into Leydig or adrenocortical cells. *Endocrinology* 147 4104-4111.

Yu J, Hu K, Smuga-Otto K, Tian S, Stewart R, Slukvin, I I & Thomson J A 2009 Human induced pluripotent stem cells free of vector and transgene sequences. *Science* 324 797-801.

Zhu M, Heydarkhan-Hagvall S, Hedrick M, Benhaim P & Zuk P 2013 Manual isolation of adipose-derived stem cells from human lipoaspirates. *Journal of visualized experiments: JoVE* e50585.

Zuk P A, Zhu M, Mizuno H, Huang J, Futrell J W, Katz A J, Benhaim P, Lorenz H P & Hedrick M H 2001 Multilineage cells from human adipose tissue: implications for cell-based therapies. *Tissue engineering* 7 211-228.

What is claimed is:

1. A method of differentiating cells, the method comprising:
    incubating mesenchymal stem cells with a combination of SF-1 and WT1 agonists and inverse agonists to induce the cells to differentiate into gonadal hormone- producing cells.

2. A method of reducing endocrine dyscrasia (dyosis) in a patient, comprising:
    maintaining or rebalancing a hypothalamic-pituitary-gonadal (HPG) axis of the patient in need thereof by administering a therapeutically effective amount of the gonadal hormone- producing cells according to the method of claim 1.

3. The method according to claim 2 wherein the ratios of hormones in the HPG axis of the patient are maintained at or near a ratio occurring during fetal life or at or near the time of greatest reproductive function of the patient.

4. The method according to claim 3 wherein the sex steroids, inhibins and follistatin of the patient are regulated to be at the ratio near the blood and/or tissue levels, production, function and activity occurring during fetal life or at or near the time of greatest reproductive function of the patient.

5. The method according to claim 3 wherein the kisspeptin, neurokinin B, dynorphin. kit ligand, AIVIH GnRH LH, FSH and activins are regulated to be at the ratio near the blood and/or tissue levels, production, function and activity occurring during fetal life or at or near the time of greatest reproductive function of the patient.

* * * * *